United States Patent [19]  [11] 4,395,276
Sikorski et al.  [45] Jul. 26, 1983

[54] THIOSULFENAMIDE DERIVATIVES OF N-PHOSPHONOMETHYLGLYCINONITRILES AS HERBICIDES

[75] Inventors: James A. Sikorski, West Lafayette, Ind.; Tommie G. Curtis, University City, Mo.

[73] Assignee: Monsanto Company, St. Louis, Mo.

[21] Appl. No.: 309,323

[22] Filed: Oct. 5, 1981

Related U.S. Application Data

[63] Continuation-in-part of Ser. No. 160,677, Jun. 18, 1980, Pat. No. 4,344,572.

[51] Int. Cl.$^3$ .......................... A01N 57/22; C07F 9/40
[52] U.S. Cl. ......................................... 71/87; 260/940; 260/968
[58] Field of Search ............................. 260/940; 71/87

[56] References Cited

U.S. PATENT DOCUMENTS

| | | | |
|---|---|---|---|
| 2,807,615 | 9/1957 | Himel | 564/102 |
| 3,731,879 | 5/1973 | Dijkhof | 239/167 |
| 3,927,832 | 12/1975 | Robison et al. | 239/168 |
| 4,008,296 | 2/1977 | Barton | 71/86 |
| 4,067,719 | 1/1978 | Dutra | 71/86 |
| 4,252,554 | 2/1981 | Dutra et al. | 71/87 |

FOREIGN PATENT DOCUMENTS

| | | | |
|---|---|---|---|
| 2256714 | 8/1975 | France | 239/168 |
| 2270774 | 12/1975 | France | 239/167 |

OTHER PUBLICATIONS

Tamotsu Fujisawa and Gen–ichi Tsuchihashi, Bulletin of the Chemical Society of Japan (1970), vol. 43, pp. 3615–3617.
Unvarified Translation of Japanese Pat. No. 142047, May 1977.

Primary Examiner—Anton H. Sutto
Attorney, Agent, or Firm—Arnold H. Cole; Howard C. Stanley; Gordon F. Sieckmann

[57] ABSTRACT

This invention relates to alkyl, cycloalkyl, aryl, and araloweralkyl thiosulfenamide derivatives of N-phosphonomethylglycinonitriles which are useful as herbicides and a process for producing the same. This invention further relates to herbicidal compositions containing such derivatives and to herbicidal methods employing such compounds and compositions.

39 Claims, No Drawings

THIOSULFENAMIDE DERIVATIVES OF N-PHOSPHONOMETHYLGLYCINONITRILES AS HERBICIDES

This invention relates to alkyl, cycloalkyl, aryl, and araloweralkyl thiosulfenamide derivatives of N-phosphonomethylglycinonitriles which are useful as herbicides and a process for producing the same. This invention further relates to herbicidal compositions containing such derivatives and to herbicidal methods employing such compounds and compositions.

U.S. Pat. No. 4,067,719 issued to Gerard A. Dutra on Jan. 10, 1978 discloses N-phosphonomethylglycinonitriles of the formula

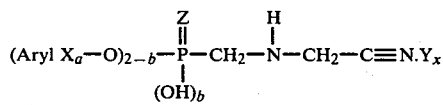

wherein (Aryl) is selected from phenyl, naphthyl or biphenylyl, each X is a substituent on said Aryl selected from halogen, alkyl of 1 to 4 carbons, alkoxy and alkylthio of 1 to 3 carbons, alkoxycarbonyl of 2 to 3 carbon atoms, methylenedioxy, cyano, trifluoromethyl or nitro, Z is oxygen or sulfur, a is an integer from zero to 3, b is an integer from zero to 1, Y is a strong acid capable of forming a salt with the amino group, and x is zero or 2, provided that x must be zero when b is 1, as well as a process for producing such compounds. These N-phosphonomethylglycinonitriles are said to be useful as herbicides.

U.S. Pat. No. 4,008,296 issued to John Edward D. Barton on Feb. 15, 1977 describes ester derivatives of N-phosphonomethylglycinonitrile having the formula

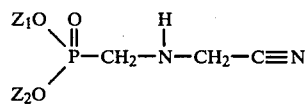

wherein $Z_1$ and $Z_2$ each represent an alkyl radical of from 1 to 6 carbon atoms; which are said to be useful as herbicides.

Japanese L.O.P. No. 142047/1977 discloses phenylcyanomethylaminomethylphosphonates of the formula

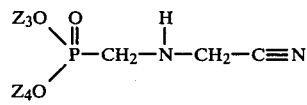

wherein $Z_3$ is hydrogen or phenyl and $Z_4$ is phenyl. Japanese L.O.P. No. 93323/1974 describes the preparation of N-(diethylphosphonomethyl)aminoacetonitrile.

U.S. Pat. No. 4,252,554 issued to Gerard A. Dutra et al on Feb. 24, 1981 discloses compounds represented by the formula

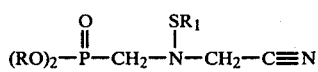

wherein R is phenyl, naphthyl or biphenylyl or phenyl, naphthyl or biphenylyl substituted with from 1 to 3 substituents independently selected from the group consisting of lower alkyl, lower alkoxy, lower alkylthio, alkoxycarbonyl, methylenedioxy, trifluoromethyl, cyano, nitro and halogen; and $R_1$ is phenyl or phenyl substituted with from 1 to 3 substituents independently selected from the group consisting of lower alkyl, lower alkoxy, halogen, trifluoromethyl and nitro.

The compounds of the present invention are represented by the formula

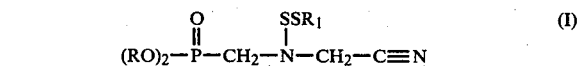

wherein R is selected from the group consisting of phenyl, naphthyl, biphenylyl; or phenyl, naphthyl or biphenylyl substituted with from 1 to 3 substituents independently selected from the group consisting of lower alkyl, lower alkoxy, lower alkylthio, lower alkoxycarbonyl, methylenedioxy, trifluoromethyl, cyano, nitro and halogen; and $R_1$ is independently alkyl, cycloalkyl, aralower alkyl, phenyl, naphthyl or phenyl or naphthyl or aralower alkyl substituted with from 1 to 3 substituents independently selected from the group consisting of lower alkyl, lower alkoxy, halogen, and trifluoromethyl.

It is preferred that R is phenyl and that $R_1$ is 1,1-dimethyl, methyl or phenylethyl.

Illustrative of the substituted phenyl groups which R and $R_1$ independently represent are mono-substituted phenyl wherein the substituent is in the ortho, meta or para position, for example, methylphenyl, butylphenyl, methoxyphenyl, butoxyphenyl, fluorophenyl, chlorophenyl, bromophenyl, iodophenyl, trifluoromethylphenyl, nitrophenyl, methylthiophenyl, butylthiophenyl, cyanophenyl, ethoxycarbonylphenyl, and the like, and the di- and tri-substituted phenyl groups wherein the substituents are the same or different and are located in the 2, 3, 4, 5 or 6 positions of the phenyl ring, for example, dichlorophenyl, dimethylphenyl, methylchlorophenyl, ethylfluorophenyl, dibutoxyphenyl, butylnitrophenyl, methylthiochlorophenyl, di(ethylthio)phenyl, trimethylphenyl, trichlorophenyl, tributylphenyl, ethyldichlorophenyl and the like.

Groups representative of a substituted naphthyl groups represented by R and $R_1$ independently include methylnaphthyl, nitronaphthyl, bromonaphthyl, dimethylnaphthyl, difluoro-naphthyl, trimethylnaphthyl and the like.

Groups representative of substituted biphenylyl groups represented by R include methylbiphenylyl, nitrobiphenylyl, bromobiphenylyl, dimethylbiphenylyl, difluorobiphenylyl, trimethylbiphenylyl and the like.

As employed herein, the term "lower alkyl" designates alkyl radicals which have from 1 to 4 carbon atoms in a straight or branched chain, such as, for example, methyl, ethyl, propyl, isopropyl, butyl, isobutyl, sec-butyl, and t-butyl.

As employed herein, the term "tertiary alkyl" includes alkyl and substituted alkyl radicals having 4 to 10 carbon atoms therein, preferably having 4 to 8 carbon atoms therein. Typically tertiary alkyl groups include tertiary butyl, tertiary amyl, tertiary hexyl, and the like.

The term "cycloalkyl" includes cyclopropane, cyclobutane, cyclopentane, cyclohexane and cyclooctane.

The term "halo" or "halogen" as employed herein means chlorine, bromine, iodine and fluorine.

The term "lower alkoxy" includes groups representative of the term "lower alkyl" in combination with oxygen and includes methoxy, ethoxy, propoxy, butoxy mixtures thereof and the like.

The term "lower alkylthio" includes representatives of lower alkyl in combination with sulfur.

The term "lower alkoxycarbonyl" includes groups representative of the aforedefined term "lower alkoxy" in combination with a carbonyl group.

In accordance with the present invention, thiosulfenamide derivatives of N-phosphonomethylglycinonitriles of formula (I) are prepared by reacting a compound of the formula

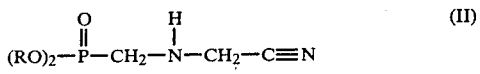

wherein R is as above defined; in an aprotic solvent, with a thiosulfenyl chloride of the formula

wherein $R_1$ is as above defined; in an aprotic solvent in the presence of a hydrogen chloride acceptor.

The reaction temperature is typically in the range from about 0° to about 100° C. However, for ease of reaction and recovery of product, it is preferred to conduct the process of the present invention within a range of about 0° to about 30° C. although greater or lower temperatures can be employed if desired.

In preparing the novel compounds of formula (I), the ratio of reactants of formulas (II) and (III), is not narrowly critical. For best results, however, for each mole of a compound of formula (II), one should employ one mole of a thiosulfenyl chloride of formula (III) to produce one mole of a compound of formula (I). It is preferred to employ an excess of thiosulfenyl chloride of formula (II) for ease of reaction and maximum yield of product of formula (I).

A hydrogen chloride acceptor is preferably used in stoichiometric excess to insure completeness of reaction. The hydrogen chloride acceptor is typically an amine, preferably a tertiary amine, which will not react with the reactants employed or products formed. Examples of suitable tertiary amine hydrogen chloride acceptors include trimethylamine, triethylamine, tributylamine, trihexylamine, 1,5-diazabicyclo-[5.4.0]-undec-5-ene, pyridine, quinoline, mixtures thereof and the like.

Due to the reactive nature of the various reaction intermediates and reactants, the process of the present invention should be conducted in an aprotic solvent under essentially anhydrous conditions. Illustrative of the aprotic solvents employed in the process of this invention include benzene, toluene, dichloromethane, tetrahydrofuran, cyclohexane, methylcyclohexane, hexane, octane, dioxane, ethyl ether, dichloromethane and the like.

While the processes of this invention can be conducted at atmospheric, sub-atmospheric or super-atmospheric pressure, for convenience and economy it is generally preferred to conduct these processes at atmospheric pressure.

Methods which may be employed for preparing compounds of formula (I) wherein $R_1$ is alkyl include those processes wherein an amine is reacted with an alkylthiosulfenyl halide. Included also are those processes wherein a halogen, an amine, and a disulfide and/or mercaptan are interacted in a single reaction step to form a thiosulfenamide. Another acceptable process includes a multistep process wherein a disulfide and/or mercaptan is reacted with a halogen to produce an organic sulfur containing halide and wherein a resulting mixture is then admixed with an amine under conditions causing reaction of halide therein with amine to produce a thiosulfenamide. The aforementioned processes are particularly described in U.S. Pat. No. 2,807,615 issued to Chester M. Himel on Sept. 24, 1957 which is incorporated herein by reference in its entirety.

Methods which may be employed for preparing compounds of formula (I) wherein $R_1$ is phenyl, naphthyl or phenyl substituted include a method for the preparation of arylthiosulfenyl chloride comprising reacting a thiophenol and sulfur dichloride such as is described in Bull Chem. Soc. Japan 43, 3615 (1970), Tamotsu Fujisawa, and Gen-ichi Tsuchihashi, which is incorporated herein in its entirety by reference.

The following illustrative, non-limiting examples will serve to further demonstrate to those skilled in the art the manner in which specific compounds within the scope of this invention can be prepared. In the examples, all parts are parts by weight unless otherwise expressly stated.

The term "lower alkyl" designates alkyl radicals which have from 1 to 4 carbon atoms in a straight or branched chain such as methyl, ethyl, propyl, isopropyl, butyl, isobutyl, sec-butyl and t-butyl.

The term "alkyl" designates alkyl radicals which have from 1 to 8 carbon atoms in a straight or branched chain and includes groups representative of the term "lower alkyl".

The term "aralower alkyl" includes combinations of these groups as aforedefined for the term "lower alkyl" with aryl groups such as phenyl, benzyl, naphthyl and biphenyl. Typical groups illustrative of "aralower alkyl" include phenylmethyl, phenylethyl, phenylpropyl, phenylbutyl and the like.

EXAMPLE I

Phosphonic Acid, [[(cyanomethyl)[(1,1-dimethylethyl)dithio]amino]methyl]-, diphenyl ester. Di-t-butyldisulfide was chlorinated according to U.S. Pat. No. 2,934,563 supra. 14.7 g of the crude product was added to a solution of N-diphenylphosphonomethylglycinonitrile (0.033 mol, 10.0 g) and triethylamine (0.033 mol, 3.4 g) in 100 ml of toluene. The resulting mixture was then stirred overnight at room temperature, filtered and concentrated to give a dark red oil. HPLC purification on 1"×13" column of oven-dried silica gel eluting with 70% cyclohexane 30% ethyl acetate gave the desired pure product as a white solid 1.4 g (10%), having a melting point of 69°-72° C. $^1$H NMR and FDMS were both consistent with pure product corresponding to a compound of formula (I) wherein R is phenyl and $R_1$ is 1,1-dimethylethyl and had an analysis for $C_{19}H_{23}N_2O_3PS_2$: Calculated: C,54.01; H,5.49; N,6.63; S,15.18 Found: C,54.42; H,5.49; N,6.72; S,15.01.

General Procedure For Preparing The Compounds Of Examples II and III

A pentane solution of tert-butylthiosulfenyl chloride was prepared as follows: Chlorine gas (3.5 ml, 0.3 mol) was condensed under nitrogen at −78° C. and then passed via double-ended needle into a solution of di-tertbutyl-disulfide (17.8 g, 0.1 mol) in 150 ml of pentane at −20° C. at such a rate that the temperature did not exceed −15° C. The resulting orange solution was then stirred at −15° C.-5° C. for 2-2.5 hours, cooled to −20° C. and added via cannula to a cold solution of the appropriate compound of formula (II) (0.03 mol) and triethylamine (10.1 g, 0.1 mol) in 150 ml of toluene at such a rate that the temperature did not exceed +5° C. The resulting yellow reaction mixture was allowed to come to room temperature over 2-3 hours, at which time thin layer chromatography indicated complete conversion to product. The precipitate of triethylamine hydrochloride was removed by filtration. The toluene filtrate was washed twice with 100 ml of cold 10% aqueous NaOH, twice with cold water, dried over MgSO$_4$, filtered and concentrated on a rotovap to give the crude product which was purified if necessary, generally on a 1"×4' column of oven-dried silica gel using 70% cyclohexane, 30% ethyl acetate as the eluent. $^1$H NMR, $^{31}$P NMR, FDMS and elemental analysis were all consistent with pure products.

EXAMPLE II

Phosphonic Acid, [[(cyanomethyl)[(1,1-dimethylethyl)dithio]amino]methyl]-, bis(4-methoxyphenyl) ester corresponding to a compound of formula (I) wherein R is p-methoxyphenyl and R$_1$ is 1,1-dimethylethyl was prepared following the aforerecited general procedure. Analysis for C$_{21}$H$_{27}$N$_2$O$_5$PS$_2$, having a melting point of 75°-78° C. was Calculated: C,52.27; H,5.64; N,5.81; S,13.29; Found: C,52.05; H,5.67; N,5.81; S,13.34.

EXAMPLE III

Phosphonic Acid, [[(cyanomethyl)[(1,1-dimethylethyl)dithio]amino]methyl]-, bis(4-chloro-3-methylphenyl) ester, corresponding to a compound of formula (I) wherein R is 4-chloro-3-methylphenyl and R$_1$ is 1,1-dimethylethyl was prepared as a white solid following the aforerecited general procedure. Analysis for C$_{21}$H$_{25}$Cl$_2$N$_2$O$_3$PS$_2$ having a melting point of 82°-84° C. was Calculated: C,48.56; H,4.85; N,5.39; S,12.35; Found: C,48.45; H,4.90; N,5.38; S,12.37.

General Procedure For Preparing Thiosulfenamide Compounds Of Examples IV and V

The appropriate tert-alkylthiosulfenyl chloride was generated in situ using the aforerecited literature methods of U.S. Pat. No. 2,807,615, supra. This solution was then transferred via double-ended needle under nitrogen into a cold toluene solution of the appropriate compound of formula (II) (0.9-1.0 equivalents) and triethylamine. The mixture was then allowed to warm to room temperature slowly. The reactions generally were complete in 2-4 hours. The mixture was then filtered to remove the triethylamine hydrochloride. The toluene filtrate was washed with equal volumes of cold 10% aqueous NaOH and cold water, dried over MgSO$_4$, and then the material was adsorbed onto silica gel. Purification by HPLC on a 1"×4' silica gel column gave the desired pure products. $^1$H NMR, $^{31}$P NMR, FDMS and elemental analyses were all consistent with pure products.

EXAMPLE IV

Phosphonic Acid, [[(cyanomethyl)[(1,1-dimethylpropyl)dithio]amino]methyl]-, diphenyl ester corresponding to a compound of formula (I) wherein R is phenyl and R$_1$ is 1,1-dimethylpropyl was prepared as a white solid having a melting point of 56°-58° C. Analysis for C$_{20}$H$_{25}$N$_2$O$_3$PS$_2$ was Calculated: C,55.03; H,5.77; N,6.42; S,14.69; Found: C,54.94; H,5.79; N,6.38; S,14.61.

EXAMPLE V

Phosphonic Acid, [[(cyanomethyl)[(1,1-dimethylethyl)dithio]amino]methyl]-, bis(2-methoxyphenyl) ester corresponding to a compound of formula (I) wherein R is 2-methoxyphenyl and R$_1$ is 1,1-dimethylethyl was prepared as a yellow oil following the aforerecited general procedure. The product had a n$_D^{25}$=1.5550, and an analysis for C$_{21}$H$_{27}$N$_2$O$_5$PS$_2$: Calculated: C,52.27; H,5.64; N,5.81; S,13.29; Found: C,52.34; H,5.68; N,5.80; S,13.28.

EXAMPLE VI

A solution of p-toluenethiosulfenyl chloride (0.05 mol) was prepared by adding p-thiocresol (6.2 g, 0.05 mol) in 100 ml of pentane to a pentane solution of sulfur dichloride (5.2 g, 0.05 mol) at $-20°$ C. The solution was allowed to warm to $+5°$ C. over 2 hours and then was added to a solution of diphenylphosphonomethyl glycinonitrile (15.0 g, 0.05 mol) and triethylamine (5.0 g, 0.05 mol) in 200 ml of toluene at 10° C. This reaction mixture was allowed to come to room temperature over a 2 hour period. The precipitate of triethylamine hydrochloride was remobed by filtration. The toluene filtrate was washed with cold aqueous 10% NaOH and cold water, dried over MgSO$_4$, filtered and then adsorbed onto silica gel. Purification by HPLC on a 1"×4' silica gel column eluting with 60% cyclohexane/40% ethyl acetate gave the desired arylthiosulfenamide product, phosphonic acid, [[(cyanomethyl)[(4-methylphenyl)dithio]amino]methyl]-, diphenyl ester as a yellow solid, corresponding to a compound of formula (I) wherein R is phenyl and R$_1$ is 4-methylphenyl, 1.2 g (5.3%), having a melting point of 63°-67° C. Analysis for C$_{22}$H$_{21}$N$_2$O$_3$P$_1$S$_2$ was: Calculated: C,57.88; H,4.64; N,6.14; S,14.05; Found: C,57.73; H,4.69; N,6.10; S,14.04.

Other compounds of this invention of formula (I) which have been prepared also include those hereafter enumerated. While these compounds have been prepared by a different process disclosed and claimed in patent application AG-2058, "Process For Preparing Thiosulfenamide Derivatives of N-phosphonomethylglycinonitriles" filed simultaneously herewith, preparation of these compounds is believed consistent with the process of this invention.

Preparation of Phosphonic acid, [[(cyanomethyl)N-chlorothio]amino]methyl]-, diphenyl ester. A solution of diphenyl-N-phosphonomethylglycinonitrile (4.5 g, 0.015 mol) and triethylamine (1.5 g, 0.015 mol) in toluene was added to a pentane solution of sulfur dichloride (1.5 g, 0.015 mol) at 0° at such a rate that the temperature did not exceed +10° C. The yellow reaction mixture was stirred at 0° C. for 45 minutes. The supernatant liquid was removed under nitrogen and concentrated in vacuo to a yellow oil which became light brown upon drying overnight on a vacuum pump. Yield 4.4 g (79%), $^{31}$P NMR ($-11.15$ ppm) having an analysis for C$_{15}$H$_{14}$Cl$_1$N$_2$O$_3$P$_1$S$_1$: Calculated C,48.85; H,3.83; N,7.60; S,8.69; Cl,9.61; Found: C,48.78; H,3.88; N,7.53; S,8.75; Cl,9.51.

General Procedure For The Preparation Of Glyphosate thiosulfenamides from phosphonic acid, [[(cyanomethyl)-N-chlorothio]amino]methyl]-diphenyl ester For Examples VII, VIII, IX, X, XI, XII and XIII hereafter following To an oven-dried 500 ml flask, cooled under nitrogen, was added 250 ml of toluene, triethylamine (0.025 mol), and the appropriate mercaptan (0.025 mol). The resulting solution was cooled to 0° C. Then a toluene solution containing phosphonic acid, [[(cyanomethyl)-N-chlorothio]amino]methyl]-diphenyl ester (0.025 mol) was added slowly via double-ended needle under nitrogen at such a rate that the reaction temperature was maintained below 10° C. When the addition was complete, the reaction mixture was stirred for 2 hours at +10° C. and then allowed to come to room temperature. The precipitate of triethylamine hydrochloride was removed by filtration. The toluene filtrate was washed with cold 10% aqueous sodium hydroxide, cold water, dried over MgSO$_4$, filtered, adsorbed onto silica gel and purified by HPLC on a 1"×4' silica gel column to give the desired glyphosate thiosulfenamides. $^1$H and $^{31}$P NMR, FDMS, and elemental analyses are all consistent with pure products.

EXAMPLE VII

Phosphonic acid, [[(cyanomethyl)(octyldithio)amino]methyl]-, diphenyl ester corresponding to a compound of formula (I) wherein R is phenyl and R$_1$ is 1-octyl was prepared using the aforerecited procedure as a brown oil having a refractive index $n_D^{25.7} = 1.5478$ and an analysis for $C_{23}H_{31}N_2O_3PS_2$: Calculated: C,57.72; H,6.53; N,5.85; S,13.39; Found: C,58.72; H,6.39; N,5.70; S,13.01.

EXAMPLE VIII

Phosphonic acid, [[(cyanomethyl)[(4-methoxyphenyl)-dithio]amino]methyl-, diphenyl ester corresponding to a compound of formula (I) wherein R is phenyl and R$_1$ is 4-methoxyphenyl was prepared using the aforerecited procedure as a yellow oil having a refractive index $n_D^{23.4} = 1.6040$ and an analysis for $C_{22}H_{21}N_2O_4PS_2$: Calculated: C,55.92; H,4.48; N,5.93; S,13.57; Found: C,55.84; H,4.52; N,5.87; S,13.62.

EXAMPLE IX

Phosphonic acid, [[(cyanomethyl)[3-(trifluoromethyl)phenyl]dithio]amino]methyl]-, diphenyl ester corresponding to a compound of formula (I) wherein R is phenyl and R$_1$ is 3-trifluoromethylphenyl was prepared using the aforerecited procedure as a yellow oil having a refractive index $n_D^{25.2} = 1.5666$ and an analysis for $C_{22}H_{18}F_3N_2O_3PS_2$: Calculated; C,51.76; H,3.55; N,5.49; S,12.56; Found: C,51.93; H,3.59; N,5.36; S,12.43.

EXAMPLE X

Phosphonic acid, [[(cyanomethyl)[(3-methylbutyl)-dithio]amino]methyl]-, diphenyl ester corresponding to a compound of formula (I) wherein R is phenyl and R$_1$ is 3-methylbutyl was prepared using the aforerecited procedure as a light yellow oil having a refractive index $n_D^{24.5} = 1.5593$ and an analysis for $C_{20}H_{25}N_2O_3PS_2$: Calculated: C,55.03; H,5.77; N,6.42; S,14.69; Found: C,55.02; H,5.80; N,6.43; S,14.63.

EXAMPLE XI

Phosphonic acid, [[(cyanomethyl)[(1-methylethyl)-dithio]amino]methyl]-, diphenyl ester corresponding to a compound of formula (I) wherein R is phenyl and R$_1$ is 1-methylethyl, (or isopropyl) was prepared using the aforerecited procedure as a light yellow oil having a refractive index $n_D^{24.8} = 1.5689$ and an analysis for $C_{18}H_{21}N_2O_3PS_2$: Calculated: C,52.93; H,5.18; N,6.86; S,15.70; Found: C,53.02; H,5.23; N,6.80, S,15.60.

EXAMPLE XII

Phosphonic acid, [[(cyanomethyl)[(methyldithio)amino]methyl]-, diphenyl ester corresponding to a compound of formula (I) wherein R is phenyl and R$_1$ is methyl was prepared using the aforerecited procedure as a yellow oil having a refractive index $n_D^{25} = 1.5759$ and an analysis for $C_{16}H_{17}N_2O_3PS_2$: Calculated: C,50.52; H,4.50; N,7.36; S,16.86 Found: C,50.62; H,4.53; N,7.35; S,16.80.

EXAMPLE XIII

Phosphonic acid, [[(cyanomethyl)[[[3-(trifluoromethyl)phenyl]methyl]dithio]amino]methyl]-, diphenyl ester corresponding to a compound of formula (I) wherein R is phenyl and R$_1$ is 3-trifluoromethylphenylmethyl was prepared using the aforerecited procedure as a yellow oil having a refractive index $n_D^{24.40};32$ 1.5640 and an analysis for $C_{23}H_{20}F_3N_2O_3PS_2$: Calculated: C,52.67; H,3.84; N,5.34; S,12.23; Found: C,52.57; H,3.84; N,5.32; S,12.20.

General Procedure For The Preparation Of thiosulfenamides from phosphonic acid, [[(cyanomethyl)-N-chlorothio]amino]methyl]-diphenyl ester For Examples XIV, XV, XVI and XVII hereafter following To an oven-dried 500 ml flask, cooled under nitrogen, is added 250 ml of toluene and cooled in an ice bath. The appropriate mercaptan and 2–3 equivalents of triethylamine was added. To this solution was added slowly via double-ended needle a toluene solution of phosphonic acid, [[(cyanomethyl)-N chlorothio]amino]-methyl]-diphenyl ester maintaining the temperature below 10° C. The reaction mixture was stirred for 3–4 hours while allowing to warm to room temperature. The triethylamine hydrochloride was removed by filtration and the filtrate was washed with cold 10% aqueous sodium hydroxide, cold water, dried over MgSO$_4$, filtered, adsorbed onto silica gel. Purification by HPLC on a 1"×4' silica gel column eluting with 30–40% ethylacetate/cyclo-hexane gave the desired thiosulfenamides. $^1$H and $^{31}$P NMR, FDMS, and elemental analyses are all consistent with pure products.

EXAMPLE XIV

Phosphonic acid, [[(cyanomethyl)(2-naphthalenyldithio)amino]methyl]-, diphenyl ester corresponding to a compound of formula (I) wherein R is phenyl and R$_1$ is 2-naphthyl was prepared using the aforerecited procedure as a light yellow solid having a melting point of 72°–75° C.

and an analysis for $C_{25}H_{21}N_2O_3PS_2$: Calculated: C,60.96; H,4.30; N,5.69; S,13.02; Found: C,61.00; H,4.34; N,5.65; S,12.96.

EXAMPLE XV

Phosphonic acid, [[(cyanomethyl)(cyclohexyldithio)amino]methyl]-, diphenyl ester corresponding to a compound of formula (I) wherein R is phenyl and R$_1$ is cyclohexyl was prepared using the aforerecited procedure as a brown oil having a refractive index $n_D^{24.2} = 1.5741$ and an analysis for $C_{21}H_{25}N_2O_3PS_2$: Calculated: C,56.36; H,5.41; N,6.26; S,14.33; Found: C,56.17; H,5.48; N,6.21; S,14.25.

EXAMPLE XVI

Phosphonic acid, [[(4-chlorophenyl)dithio](cyanomethyl)amino]methyl]-, diphenyl ester corresponding to a compound of formula (I) wherein R is phenyl and $R_1$ is 4-chlorophenyl was prepared using the aforerecited procedure as a brown solid having a melting point of 50°–55° C. and an analysis $C_{21}H_{18}ClN_2O_3PS_2$: Calculated: C,52.89; H,3.81; N,5.87; S,13.44; Found: C,52.65; H,3.91; N,5.83; S,13.36.

EXAMPLE XVII

Phosphonic acid, [[(cyanomethyl)[(2-phenylethyl)dithio]amino]methyl]-, diphenyl ester corresponding to a compound of formula (I) wherein R is phenyl and $R_1$ is 2-phenylethyl was prepared using the aforerecited procedure as a brown oil having a refractive index $n_D^{25} = 1.5948$ and an analysis for $C_{23}H_{23}N_2O_3PS_2$: Calculated: C,58.71; H,4.93; N,5.95; S,13.63; Found: C,58.48; H,4.98; N,5.92; S,13.56.

EXAMPLE XVIII

An oven-dried 500 ml flask cooled under nitrogen was charged with 150 ml of toluene, cooled to $-20°$ C., and sulfur dichloride (5.1 g, 0.05 mol) was added. To this solution was added slowly via cannula a solution of diphenylphosphonomethylglycinonitrile (15 g, 0.05 mol) and excess triethylamine in 150 ml of toluene, at such a rate to maintain the temperature below $-10°$ C. The reaction mixture was stirred at $-20°$ C. for 3 hours. The supernatant liquid, a toluene solution of phosphonic acid, [[(cyanomethyl)-N-chlorothio-amino)methyl]-, diphenyl ester was removed under nitrogen and added slowly via cannula over a 2 hour period to a solution of tert-butyl mercaptan (4.5 g, 0.05 mol) and excess triethylamine in 100 ml of toluene at $-20°$ C. After 30 minutes the precipitate of triethylamine hydrochloride was removed by filtration and the filtrate was washed with cold 10% aqueous NaOH followed by cold water, dried over $MgSO_4$, filtered, and concentrated in vacuo. Purification by HPLC on a Waters Prep Pak 500 silica gel column, eluting with 20% ethyl acetate, 80;1 % cyclohexane, followed by recrystallization from methylene chloride, petroleum ether gave 3.3 g of tan solid, having a melting point of 87°–88° C., corresponding to a compound of formula (I) wherein R is phenyl and $R_1$ is tertiary butyl and having an analysis Calculated: C,54.01; H,5.49; N,6.63; S,15.15; Found: C,53.93; H,5.52; N,6.60; S,15.13.

This product corresponds to the product of Example I hereof.

EXAMPLE XIX

The post-emergence herbicidal activity of some of the various compounds of this invention was demonstrated by greenhouse testing in the following manner. A good grade of top soil is placed in aluminum pans having holes in the bottom and compacted to a depth of 0.95 to 1.27 cm. from the top of the pan. A predetermined number of seeds of each of several dicotyledonous and monocotyledonous annual plant species and/or vegetative propagules for the perennial plant species are placed on the soil and pressed into the soil surface. The seeds and/or vegetative propagules are covered with soil and leveled. The pans are then placed on a sand bench in the greenhouse and watered from below as needed. After the plants reach the desired age (two to three weeks), each pan except for the control pans is removed individually to a spraying chamber and sprayed by means of an atomizer operating at a positive air pressure of approximately 1.46 kg/cm² absolute. The atomizer contains 6 ml. of a solution or suspension of the chemical. In that 6 ml., is an amount of a cyclohexanone emulsifying agent mixture to give a spray solution or suspension which contains about 0.4% by weight of the emulsifier. The spray solution or suspension contains a sufficient amount of the candidate chemical in order to give application rates corresponding to those set forth in the tables. The spray solution is prepared by taking an aliquot of a 1.0% by weight stock solution or suspension of the candidate chemical in an organic solvent such as acetone or tetrahydrofuran or in water. The emulsifying agent employed is a mixture comprising 35 weight percent butylamine dodecylbenzene sulfonate and 65 weight percent of a tall oil ethylene oxide condensate having about 11 moles of ethylene oxide per mole of tall oil. The pans are returned to the greenhouse and watered as before and the injury to the plants as compared to the control is observed at approximately two and four weeks as indicated in the tables under WAT and the results recorded. In some instances, the two-week observations are omitted.

The post-emergence herbicidal activity index used in Table I is as follows:

| Plant Response | Index |
| --- | --- |
| 0–24% control | 0 |
| 25–49% control | 1 |
| 50–74% control | 2 |
| 75–99% control | 3 |
| 100% control | 4 |

The plant species utilized in these tests are identified by letter in accordance with the following legend:

| | |
| --- | --- |
| A - Canada Thistle* | K - Barnyardgrass |
| B - Cocklebur | L - Soybean |
| C - Velvetleaf | M - Sugar Beet |
| D - Morningglory | N - Wheat |
| E - Lambsquarters | O - Rice |
| F - Smartweed | P - Sorghum |
| G - Yellow Nutsedge* | Q - Wild Buckwheat |
| H - Quackgrass* | R - Hemp Sesbania |
| I - Johnsongrass* | S - Panicum Spp |
| J - Downy Brome | T - Crabgrass |

*Established from vegetative propagules.
A dash (-) in the tables indicates that the particular species was absent in the test.

TABLE I

| Compound of Example No. | WAT | kg/h | A | B | C | D | E | F | G | H | I | J | K |
| --- | --- | --- | --- | --- | --- | --- | --- | --- | --- | --- | --- | --- | --- |
| I | 4 | 11.2 | 3 | 4 | 3 | 4 | 4 | 4 | 2 | 1 | 2 | 1 | 3 |
|   | 4 | 5.6 | 2 | 4 | 4 | 4 | 4 | 4 | 1 | 1 | 2 | 3 | 3 |
| II | 4 | 11.2 | — | 4 | 4 | 2 | 4 | 2 | 2 | 1 | 2 | 4 | 2 |
|   | 4 | 5.6 | — | 3 | 3 | 2 | 3 | 1 | 1 | 4 | 3 | 3 | 2 |
| III | 4 | 11.2 | — | 2 | 0 | 0 | 3 | 1 | 0 | 0 | 4 | 0 | 1 |
|   | 4 | 5.6 | — | 1 | 0 | 0 | 0 | 0 | 0 | 0 | — | 0 | 0 |

TABLE I-continued

| Compound of Example No. | WAT | kg/h | A | B | C | D | E | F | G | H | I | J | K |
|---|---|---|---|---|---|---|---|---|---|---|---|---|---|
| IV | 4 | 11.2 | 1 | 2 | 1 | 2 | 4 | 1 | 2 | 1 | 2 | 1 | 3 |
|  | 4 | 5.6 | 2 | 1 | 1 | 2 | 4 | 0 | 2 | 2 | 0 | 1 | 2 |
| V | 4 | 11.2 | 0 | 1 | 0 | 2 | 1 | 0 | 0 | 0 | 0 | 0 | 1 |
|  | 2 | 5.6 | 0 | 1 | 0 | 1 | 1 | 0 | 0 | 0 | 0 | 0 | 0 |
| VI | 4 | 11.2 | 1 | 2 | 0 | 2 | 4 | 0 | 2 | 2 | 4 | 0 | 2 |
|  | 4 | 5.6 | 0 | 1 | 0 | 1 | 2 | 0 | 2 | 1 | 3 | 0 | 2 |
| VII | 4 | 11.2 | 1 | 2 | 1 | 2 | 3 | 1 | 2 | 1 | 2 | 0 | 2 |
|  | 4 | 5.6 | 1 | 2 | 1 | 2 | 3 | 0 | 2 | 0 | 3 | 1 | 1 |
| VIII | 4 | 11.2 | 2 | 2 | 1 | 2 | 4 | 0 | 2 | 1 | 2 | 2 | 2 |
|  | 4 | 5.6 | 2 | 1 | 1 | 1 | 3 | — | 1 | 0 | 2 | 0 | 2 |
| IX | 2 | 11.2 | 1 | 2 | 0 | 1 | 3 | 1 | 1 | 0 | 1 | 0 | 2 |
|  | 4 | 11.2 | 1 | 2 | 1 | 2 | 4 | 4 | 2 | 0 | 1 | 2 | 2 |
|  | 2 | 5.6 | 1 | 1 | 0 | 1 | 3 | 0 | 1 | 1 | 2 | 1 | 2 |
|  | 4 | 5.6 | 2 | 2 | 1 | 3 | 3 | 0 | 2 | 2 | 3 | 1 | 2 |
| X | 4 | 11.2 | 1 | 3 | 0 | 2 | 3 | 3 | 2 | 2 | 3 | 2 | 3 |
|  | 4 | 5.6 | 2 | 2 | 1 | 2 | 4 | 1 | 2 | 1 | 1 | 2 | 2 |
| XI | 4 | 11.2 | 2 | 2 | 2 | 2 | 4 | 2 | 3 | 1 | 3 | 3 | 2 |
|  | 4 | 5.6 | 2 | 2 | 1 | 2 | 3 | 2 | 0 | 0 | 3 | 2 | 2 |
| XII | 4 | 11.2 | 4 | 3 | 1 | 2 | 4 | 4 | 2 | 1 | 4 | 2 | 3 |
|  | 4 | 5.6 | 4 | 2 | 1 | 2 | 3 | 2 | 2 | 2 | 3 | 3 | 2 |
| XIII | 4 | 11.2 | — | 2 | 1 | 1 | 4 | 0 | 2 | 0 | 3 | 2 | 2 |
|  | 4 | 5.6 | — | 1 | 1 | 1 | 4 | 0 | 2 | — | 3 | 1 | 2 |
| XIV | 4 | 11.2 | — | 1 | 1 | 0 | 3 | 3 | 0 | 1 | 1 | 0 | 1 |
|  | 2 | 5.6 | — | 0 | 1 | 0 | 1 | 0 | 0 | 0 | 1 | 0 | 0 |
| XV | 4 | 11.2 | — | 2 | 1 | 1 | 3 | 0 | 0 | 0 | 1 | 1 | 1 |
|  | 2 | 5.6 | — | 0 | 1 | 0 | 3 | 0 | 0 | 0 | 0 | 0 | 0 |
| XVI | 4 | 11.2 | — | 3 | 2 | 1 | 4 | 2 | 1 | 2 | 2 | 1 | 3 |
|  | 4 | 5.6 | — | 0 | 0 | 0 | 0 | 0 | 0 | 0 | 0 | 0 | 0 |
| XVII | 4 | 11.2 | — | 4 | 2 | 1 | 4 | 3 | 2 | 3 | 4 | 3 | 2 |
|  | 4 | 5.6 | — | 2 | 0 | 1 | 4 | 0 | 2 | 0 | 1 | 0 | 2 |

TABLE II

| Compound of Example No. | WAT | kg/h | L | M | N | O | P | B | Q | D | R | E | F | C | J | S | K | T |
|---|---|---|---|---|---|---|---|---|---|---|---|---|---|---|---|---|---|---|
| I | 4 | 5.6 | 2 | 3 | 2 | 3 | 4 | — | 2 | 4 | — | 4 | 4 | 3 | 2 | 4 | 3 | 4 |
|  | 4 | 1.12 | 1 | 0 | 1 | 1 | 2 | — | 1 | 1 | 4 | 4 | 4 | 2 | 1 | 3 | 2 | 3 |
|  | 4 | 0.28 | 1 | 0 | 1 | 0 | 2 | — | 1 | 1 | 0 | 1 | 1 | 0 | 0 | 1 | 1 | 1 |
|  | 2 | 0.06 | 0 | 0 | 0 | 0 | 0 | — | 0 | 0 | 0 | 0 | 0 | 0 | 0 | 0 | 0 | 0 |
| II | 4 | 5.6 | 1 | 1 | 1 | 2 | 2 | 3 | 2 | 2 | 1 | 4 | 2 | 1 | 2 | 1 | 2 | — |
|  | 4 | 1.12 | 1 | 0 | 1 | 0 | 2 | 1 | 2 | 2 | 0 | 1 | 1 | 0 | 2 | 1 | 1 | — |
|  | 2 | 0.28 | 0 | 0 | 0 | 0 | 1 | 1 | 1 | 1 | 0 | 0 | 0 | 0 | — | 0 | 0 | — |
| IX | 4 | 5.6 | 1 | 0 | 1 | 2 | 3 | 3 | 2 | 2 | 1 | 4 | 2 | 1 | 1 | 2 | 3 | 3 |
|  | 4 | 1.12 | 1 | 0 | 0 | 0 | 2 | 1 | 0 | 1 | 0 | 2 | 1 | 0 | 0 | 0 | 0 | 3 |
| X | 4 | 5.6 | 2 | 1 | 1 | 1 | 3 | 3 | 1 | 2 | 1 | 3 | 1 | 2 | 2 | 1 | 3 | 3 |
|  | 4 | 1.12 | 1 | 1 | 0 | 0 | 2 | 1 | 0 | 1 | 0 | 1 | 0 | 0 | 2 | 0 | 1 | 1 |
| XI | 2 | 5.6 | 1 | 0 | 1 | 0 | 2 | 2 | 1 | 1 | 1 | 3 | — | 1 | 2 | 1 | 2 | 3 |
|  | 4 | 5.6 | 1 | 1 | 1 | 0 | 3 | 3 | 1 | 1 | 1 | 3 | — | 2 | 2 | 1 | 3 | 3 |
|  | 2 | 1.12 | 0 | 0 | 1 | 0 | 1 | 1 | 0 | 1 | 0 | 3 | — | 0 | 0 | 0 | 1 | 1 |
|  | 4 | 1.12 | 0 | 0 | 0 | 0 | 1 | 1 | 0 | 0 | 0 | 3 | — | 1 | 0 | 0 | 0 | 1 |
|  | 4 | 0.28 | 0 | 0 | 0 | 0 | 0 | 0 | 0 | 0 | 0 | 0 | — | 0 | 0 | 0 | 0 | 1 |
| XII | 2 | 5.6 | 2 | 1 | 2 | 3 | 2 | 2 | 2 | 2 | 1 | 3 | — | 2 | 1 | 1 | 3 | 4 |
|  | 4 | 5.6 | 2 | 1 | 3 | 3 | 3 | 3 | 3 | 2 | 1 | 4 | — | 2 | 1 | 2 | 3 | 4 |
|  | 2 | 1.12 | 1 | 0 | 1 | 0 | 1 | 1 | 0 | 1 | 0 | 1 | — | 1 | 1 | 0 | 1 | 3 |
|  | 4 | 1.12 | 1 | 0 | 0 | 0 | 2 | 1 | 0 | 0 | 0 | 0 | — | 0 | 0 | 0 | 1 | 3 |
|  | 2 | 0.28 | 0 | 0 | 1 | 0 | 1 | 1 | 1 | 1 | 0 | 1 | — | 0 | 0 | 0 | 0 | 1 |
|  | 2 | 0.056 | 0 | 0 | 0 | 0 | 0 | 0 | 0 | 0 | 0 | 0 | — | 0 | 0 | 0 | 0 | 0 |
| XIV | 2 | 5.6 | 0 | 0 | 1 | 0 | 1 | 1 | 1 | 1 | 1 | 3 | 1 | 0 | 0 | 0 | 1 | 2 |
|  | 2 | 1.12 | 0 | 0 | 0 | 0 | 0 | 0 | 0 | 0 | 0 | 0 | 0 | 0 | 0 | 0 | 0 | 0 |
|  | 2 | 0.28 | 0 | 0 | 0 | 0 | 0 | 0 | 0 | 0 | 0 | 0 | 0 | 0 | 0 | 0 | 0 | 0 |
| XVI | 2 | 5.6 | 1 | 3 | 2 | 1 | 1 | 3 | 3 | 1 | 1 | 3 | 1 | 3 | 1 | 1 | 1 | 3 |
|  | 2 | 1.12 | 0 | 1 | 0 | 0 | 0 | 0 | 0 | 0 | 0 | 0 | 0 | 0 | 0 | 0 | 0 | 0 |
| XVII | 4 | 5.6 | 1 | 1 | 1 | 0 | 3 | 2 | 2 | 1 | 1 | 3 | 2 | 2 | 2 | 1 | 2 | 3 |
|  | 4 | 1.12 | 0 | 0 | 0 | 0 | 1 | 0 | 0 | 0 | 0 | 0 | 0 | 0 | 0 | 0 | 0 | 0 |
|  | 2 | 0.28 | 0 | 0 | 0 | 0 | 0 | 0 | 0 | 0 | 0 | 0 | 0 | 0 | 0 | 0 | 0 | 0 |

From the test results presented in Tables I and II, it can be seen that the post-emergent herbicidal activity of the compounds of this invention is, for the most part, general in nature. In certain specific instances, however, some selectivity is demonstrated. In this regard it should be recognized that each individual species selected for the above tests is a representative member of a recognized family of plant species.

The herbicidal compositions, including concentrates which require dilution prior to application to the plants, of this invention contain from 5 to 95 parts by weight of at least one compound of this invention and from 5 to 95 parts by weight of an adjuvant in liquid or solid form, for example, from about 0.25 to 25 parts by weight of wetting agent, from about 0.25 to 25 parts by weight of a dispersant and from 4.5 to about 94.5 parts by weight of inert liquid extender, e.g., water, acetone, tetrahydrofuran, all parts being by weight of the total composition.

Preferably, the compositions of this invention contain from 5 to 75 parts by weight of at least one compound of this invention, together with the adjuvants. Where required, from about 0.1 to 2.0 parts by weight of the inert liquid extender can be replaced by a corrosion inhibitor such as ethanol mercaptan, sodium thiosulfate, dodecylmono or dimercaptan or anti-foaming agent such as a dimethylpolysiloxane, or both. The compositions are prepared by admixing the active ingredient with an adjuvant including diluents, extenders, carriers and conditioning agents to provide compositions in the form of finely-divided particulate solids, pellets, solutions, dispersions or emulsions. Thus, the active ingredient can be used with an adjuvant such as a finely-divided solid, a liquid of organic origin, water, a wetting agent, a dispersing agent, an emulsifying agent or any suitable combination of these.

The herbicidal compositions of this invention, particularly liquids and soluble powders, preferably contain as a conditioning agent one or more surface-active agents in amounts sufficient to render a given composition readily dispersible in water or in oil. The incorporation of a surface-active agent into the compositions greatly enhances their efficacy. By the term "surface-active agent", it is understood that wetting agents, dispersing agents, suspending agents and emulsifying agents are included therein. Anionic, cationic and non-ionic agents can be used with equal facility.

Preferred wetting agents are alkyl benzene and alkyl naphthalene sulfonates, sulfated fatty alcohols, amines or acid amides, long chain acid esters of sodium isothionate, esters of sodium sulfosuccinate, sulfated or sulfonated fatty acid esters petroleum sulfonates, sulfonated vegetable oils, polyoxyethylene derivatives of phenols and alkylphenols (particularly isooctylphenol and nonylphenol) and polyoxyethylene derivatives of the mono-higher fatty acid esters of hexitol anhydrides (e.g., sorbitan). Preferred dispersants are methyl cellulose, polyvinyl alcohol, sodium lignin, sulfonates, polymeric alkyl napthalene sulfonates, sodium naphthalene sulfonate, polymethylene bisnaphthalenesulfonate and sodium N-methyl-N-(long chain acid) taurates.

When operating in accordance with the present invention, effective amounts of the compounds or compositions of this invention are applied to the plants, or to soil containing the plants, or are incorporated into aquatic media in any convenient fashion. The application of liquid and particulate solid compositions to plants or soil can be carried out by conventional methods, e.g., power dusters, boom and hand sprayers and spray dusters. The compositions can also be applied from airplanes as a dust or a spray because of their effectiveness at low dosages. The application of herbicidal compositions to aquatic plants is usually carried out by adding the compositions to the aquatic media in the area where control of the aquatic plants is desired.

The application of an effective amount of the compounds or compositions of this invention to the plant is essential and critical for the practice of the present invention. The exact amount of active ingredient to be employed is dependent upon the response desired in the plant as well as such other factors as the plant species and stage of development thereof, and the amount of rainfall as well as the specific glycine employed. In foliar treatment for the control of vegetative growth, the active ingredients are applied in amounts from about 0.112 to about 56.0 or more kilograms per hectare. In pre-emergent treatments, the rate of application can be from about 5.6 to about 22.4 or more kilograms per hectare. In applications for the control of aquatic plants, the active ingredients are applied in amounts of from about 1.0 parts per million to about 1000 parts per million, based on the aquatic medium. An effective amount for phytotoxic or herbicidal control is that amount necessary for overall or selective control, i.e., a phytotoxic or herbicidal amount. It is believed that one skilled in the art can readily determine from the teachings of this specification, including examples, the approximate application rate.

There are several possible methods for applying liquid compositions of this invention to emerged plants. Such methods include the use of wiper systems whereby the plant to be treated is contacted with an absorbent material containing the particular liquid composition, a portion of which is thereby released onto the plant upon contact therewith. Such wiper systems typically comprise a reservoir of the liquid composition into which a portion of the absorbent material is placed and is fed therethrough. Generally, substances employable as absorbent material include substances of any shape or form capable of absorbing the liquid composition and releasing a portion of the same upon contact with the plant. Typical absorbent materials include felt, foam rubber, cellulose, nylon, sponges, hemp, cotton, burlap, polyester over acrylic, combinations thereof and the like. Forms of absorbent material include rope, twine, string, cloths, carpets, combinations thereof and the like. These forms may be assembled in any manner desired including a pipe rope wick, a wedge rope wick, a multi-rope wick and the like.

In another possible application method, liquid compositions may be selectively applied to weeds by the use of recirculating sprayer systems wherein the recirculating spray unit is mounted on a tractor or high clearance mobile equipment and the spray is directed horizontally onto the weeds growing with a crop. Spray not intercepted by the weeds is collected in a recovery chamber before contacting the crop and is reused. Roller applications may also be employed to apply liquid compositions to weeds growing over a crop.

In yet another possible application method, shielded applicators may be employed to direct the liquid composition in the form of a spray onto the weeds while effectively shielding the crops from the spray.

These and other possible application methods for selectively applying liquid compositions to weeds are discussed in detail in Innovative Methods of Post-Emergence Weed Control, McWhorter C. G., Southern Weed Science Society, 33rd Annual Meeting Proceedings, Jan. 15-17, 1980; Auburn University Printing Service, Auburn, Alabama U.S.A., the teachings of which are incorporated herein by reference in their entirety.

Another possible method of applying liquid compositions of this invention to plants includes controlled droplet application which is also known as the ultra low-volume chemical application. Controlled droplet application involves the production of uniform or nearly uniform spray drops of a predetermined size and the conveyance of these drops with negligible evaporation to a spray target. In particular, this method comprises feeding spray solutions to a rotary atomizer comprising a small dusk with serrated edges that disperses liquid into droplets as the disk spins. Different droplet sizes are produced by changing solution flow rates to the spinning disk or changing the speed of rotation of the disk.

Those of skill in the art will recognize that the physical and chemical characteristics of the compound or composition employed will determine to a large extent the particular application method selected therewith.

The aforementioned and other methods for applying liquid compositions to plants are discussed in detail in "Rope Wick Applicator-Tool With A Future", Dale, James E., pp. 3-4, "The Recirculating Sprayer and Roundup ® Herbicide", Derting, Claude W., pp. 5-7, and "C.D.A. Herbicide Application", McGarvey, Frank X., *Weeds Today,* Volume 11, Number 2, pp. 8-9, Late Spring, 1980, 309 W. Clark St., Champaign, Ill., the teachings of which are incorporated herein by reference in their entirety.

Although this invention has been described with respect to specific modifications, the details thereof are not to be construed as limitations, for it will be apparent that various equivalents, changes and modifications may be resorted to without departing from the spirit and scope thereof and it is understood that such equivalent embodiments are intended to be included herein.

What is claimed is:

1. A method of controlling undesired plants which comprises applying to said plants or plant growth medium a herbicidally effective amount of a compound of the formula

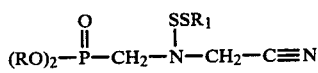

wherein R is selected from the group consisting of phenyl, naphthyl or biphenylyl; or phenyl, naphthyl or biphenylyl substituted with from 1 to 3 substituents independently selected from the group consisting of lower alkyl, lower alkoxy, lower alkylthio, alkoxycarbonyl, methylenedioxy, trifluoromethyl, cyano, nitro and halogen; and $R_1$ is alkyl, aralower alkyl, cycloalkyl, naphthyl or phenyl or naphthyl or aralower alkyl substituted with from 1 to 3 substituents independently selected from the group consisting of lower alkyl, lower alkoxy, halogen, and trifluoromethyl.

2. A method according to claim 1 wherein R is phenyl or phenyl substituted.

3. A method according to claim 2 wherein $R_1$ is phenyl or phenyl substituted with from 1 to 3 substituents independently selected from the group consisting of lower alkyl, lower alkoxy, halogen and trifluoromethyl.

4. A method according to claim 2 wherein $R_1$ is alkyl or cycloalkyl or aralower alkyl.

5. A method according to claim 4 wherein $R_1$ is isopropyl.

6. A method according to claim 4, wherein $R_1$ is tertiary butyl.

7. A method according to claim 4, wherein $R_1$ is n-octyl.

8. A method according to claim 4, wherein $R_1$ is cyclohexyl.

9. A method according to claim 4, wherein $R_1$ is phenylethyl.

10. A method according to claim 4 wherein said compound is phosphonic acid, [[(cyanomethyl)[(1,1-dimethylethyl)dithio]amino]methyl]-, diphenyl ester.

11. A method according to claim 4 wherein said compound is phosphonic acid, [[(cyanomethyl)[(1,1-dimethylethyl)dithio]amino]methyl]-, bis(4-methoxyphenyl)ester.

12. A method according to claim 4 wherein said compound is phosphonic acid, [[(cyanomethyl)[(methyl)dithio]amino]methyl]-, diphenyl ester.

13. A method according to claim 4 wherein said compound is phosphonic acid, [[(cyanomethyl)[(2-phenylethyl)dithio]amino]methyl]-, diphenyl ester.

14. A compound of the formula

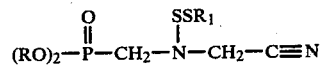

wherein R is selected from the group consisting of phenyl, naphthyl or biphenylyl; or phenyl, naphthyl or biphenylyl substituted with from 1 to 3 substituents independently selected from the group consisting of lower alkyl, lower alkoxy, lower alkylthio, alkoxycarbonyl, methylenedioxy, trifluoromethyl, cyano, nitro and halogen; and $R_1$ is independently alkyl, aralower alkyl, cycloalkyl, phenyl, naphthyl or phenyl or naphthyl or aralower alkyl substituted with from 1 to 3 substituents independently selected from the group consisting of lower alkyl, lower alkoxy, halogen, and trifluoromethyl.

15. A compound according to claim 14 wherein R is phenyl or phenyl substituted.

16. A compound according to claim 15 wherein $R_1$ is phenyl or phenyl substituted with from 1 to 3 substituents independently selected from the group consisting of lower alkyl, lower alkoxy, halogen and trifluoromethyl.

17. A compound according to claim 15 wherein $R_1$ is alkyl or cycloalkyl or aralower alkyl.

18. A compound according to claim 17 wherein $R_1$ is isopropyl.

19. A compound according to claim 17 wherein $R_1$ is tertiary butyl.

20. A compound according to claim 17 wherein $R_1$ is n-octyl.

21. A compound according to claim 17 wherein $R_1$ is cyclohexyl.

22. A compound according to claim 17 wherein $R_1$ is phenylethyl.

23. A compound according to claim 17 wherein the compound is phosphonic acid, [[(cyanomethyl)[(1,1-dimethylethyl)dithio]amino]methyl]-, diphenyl ester.

24. A compound according to claim 17 wherein the compound is phosphonic acid, [[(cyanomethyl)[(1,1-dimethylethyl)dithio]amino]methyl]-, bis(4-methoxyphenyl)ester.

25. A compound according to claim 17 wherein the compound is phosphonic acid, [[(cyanomethyl)[(methyl)dithio]amino]methyl]-, diphenyl ester.

26. A compound according to claim 17 wherein the compound is phosphonic acid, [[(cyanomethyl)[(2-phenylethyl)dithio]amino]methyl]-, diphenyl ester.

27. A herbicidal composition comprising an inert adjuvant and a herbicidally effective amount of a compound of the formula

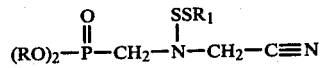

wherein R is selected from the group consisting of phenyl, naphthyl or biphenylethyl; or phenyl, naphthyl or biphenylyl substituted with from 1 to 3 substituents independently selected from the group consisting of lower alkyl, lower alkoxy, lower alkylthio, alkoxycarbonyl, methylenedioxy, trifluoromethyl, cyano, nitro and halogen; and $R_1$ is alkyl, aralower alkyl, cycloalkyl, naphthyl or phenyl or phenyl or naphthyl or aralower alkyl substituted with from 1 to 3 substituents independently selected from the group consisting of lower alkyl, lower alkoxy, halogen, and trifluoromethyl.

28. A composition according to claim 27 wherein said compound is a compound wherein R is phenyl or phenyl substituted.

29. A composition according to claim 28 wherein said compound is a compound wherein $R_1$ is phenyl or phenyl substituted with from 1 to 3 substituents independently selected from the group consisting of lower alkyl, lower alkoxy, halogen and trifluoromethyl.

30. A composition according to claim 28 wherein said compound is a compound wherein $R_1$ is alkyl or cycloalkyl or aralower alkyl.

31. A composition according to claim 30 wherein $R_1$ is isopropyl.

32. A composition according to claim 30 wherein $R_1$ is tertiary butyl.

33. A composition according to claim 30 wherein $R_1$ is n-octyl.

34. A composition according to claim 30 wherein $R_1$ is cyclohexyl.

35. A composition according to claim 30 wherein $R_1$ is phenylethyl.

36. A composition according to claim 30 wherein said compound is phosphonic acid, [[(cyanomethyl)[1,1-dimethylethyl)dithio]amino]methyl]-, diphenyl ester.

37. A composition according to claim 30 wherein said compound is phosphonic acid, [[(cyanomethyl)[(1,1-dimethylethyl)dithio]amino]methyl]-, bis(4-methoxyphenyl)ester.

38. A composition according to claim 30 wherein said compound is phosphonic acid, [[(cyanomethyl)[(methyl)dithio]amino]methyl]-, diphenyl ester.

39. A composition according to claim 30 wherein said compound is phosphonic acid, [[(cyanomethyl)[(2-phenyl-ethyl)dithio]amino]methyl]-, diphenyl ester.

* * * * *

UNITED STATES PATENT AND TRADEMARK OFFICE
CERTIFICATE OF CORRECTION

PATENT NO. : 4,395,276
DATED : July 26, 1983
INVENTOR(S) : James A. Sikorski and Tommie G. Curtis It is certified that error appears in the above-identified patent and that said Letters Patent are hereby corrected as shown below:

Column 2, line 26 - "dimethyl" should be "dimethylethyl"

Column 3, line 36 - "formula (II)" should be "formula (III)"

Column 8, line 20 - ";32" should be "="

Column 9, line 43 - "80;1%" should be "80%"

Claim 27, Column 16, line 66 - "biphenylethyl" should be "biphenylyl"

Signed and Sealed this

Tenth Day of January 1984

[SEAL]

Attest:

GERALD J. MOSSINGHOFF

Attesting Officer

Commissioner of Patents and Trademarks